US009125563B2

(12) United States Patent
Abrams et al.

(10) Patent No.: US 9,125,563 B2
(45) Date of Patent: Sep. 8, 2015

(54) SIGNAL MONITORING SYSTEM INCLUDING EMI-SHIELDING COUPLER

(71) Applicant: CAS Medical Systems, Inc., Branford, CT (US)

(72) Inventors: Roy Abrams, Branford, CT (US);
Karen Duffy, Orange, CT (US);
Matthew Dalene, Clinton, CT (US);
William Kosturko, Milford, CT (US);
John Gamelin, Avon, CT (US)

(73) Assignee: CAS Medical Systems, Inc., Branford, CT (US)

( * ) Notice: Subject to any disclaimer, the term of this patent is extended or adjusted under 35 U.S.C. 154(b) by 23 days.

(21) Appl. No.: 14/061,308

(22) Filed: Oct. 23, 2013

(65) Prior Publication Data

US 2014/0121481 A1    May 1, 2014

Related U.S. Application Data

(60) Provisional application No. 61/717,401, filed on Oct. 23, 2012.

(51) Int. Cl.
| *H01R 13/658* | (2011.01) |
| *A61B 5/00* | (2006.01) |
| *A61B 5/1455* | (2006.01) |
| *H01R 13/6598* | (2011.01) |

(52) U.S. Cl.
CPC ........... *A61B 5/0075* (2013.01); *A61B 5/14552* (2013.01); *A61B 5/743* (2013.01); *A61B 2562/182* (2013.01); *A61B 2562/228* (2013.01); *H01R 13/6598* (2013.01)

(58) Field of Classification Search
CPC ..... H01R 13/658; H01R 9/032; H01R 12/775
USPC ........................................ 439/607.47–607.49
See application file for complete search history.

(56) References Cited

U.S. PATENT DOCUMENTS

| 4,684,199 | A | * | 8/1987 | Ezure et al. .............. 439/607.47 |
| 5,380,223 | A | * | 1/1995 | Marsh et al. ............. 439/607.48 |
| 5,667,407 | A | * | 9/1997 | Frommer et al. ........ 439/607.48 |
| 5,725,395 | A | * | 3/1998 | Lee .......................... 439/607.48 |
| 5,934,925 | A | | 8/1999 | Tobler et al. |
| 6,152,754 | A | | 11/2000 | Gerhardt et al. |
| 6,257,914 | B1 | | 7/2001 | Comerci et al. |
| 6,280,252 | B1 | * | 8/2001 | Huang ...................... 439/607.48 |
| 6,290,542 | B1 | * | 9/2001 | Kuo ......................... 439/607.49 |
| 6,595,801 | B1 | * | 7/2003 | Gardner et al. .......... 439/607.55 |
| 7,637,779 | B2 | * | 12/2009 | Nagata et al. ............ 439/607.49 |
| 8,007,317 | B2 | * | 8/2011 | Su et al. ................... 439/607.46 |
| 8,075,341 | B2 | * | 12/2011 | Su et al. ................... 439/607.48 |

(Continued)

*Primary Examiner* — Gary Paumen
(74) *Attorney, Agent, or Firm* — O'Shea Getz P.C.

(57) ABSTRACT

An apparatus for electrically and mechanically coupling a connection portion of a sensor assembly with a connection portion of an interface cable is provided. The apparatus includes a frame having an EMI shielding material. The frame defines a first port operable to engage the connection portion of the sensor assembly and a second port operable to engage the connection portion of the interface cable. The frame includes attachment features operable to mechanically secure the connection portion of the sensor assembly and the connection portion of the interface cable relative to the frame. The frame is configured to provide a Faraday Cage around substantially all of the connection portion of the sensor assembly and the connection portion of the interface cable when the connection portions are in coupled configuration.

20 Claims, 7 Drawing Sheets

(56) References Cited

U.S. PATENT DOCUMENTS

| | | | |
|---|---|---|---|
| 8,727,803 B2 * | 5/2014 | Kurachi | 439/497 |
| 8,794,995 B2 * | 8/2014 | Wu | 439/497 |
| 2002/0045385 A1 * | 4/2002 | Wang | 439/610 |
| 2010/0216342 A1 * | 8/2010 | Lin | 439/607.49 |

* cited by examiner

SIGNAL MONITORING SYSTEM INCLUDING EMI-SHIELDING COUPLER

BACKGROUND OF THE INVENTION

1. Technical Field

This invention relates to signal monitoring systems in general, and in particular to signal monitoring systems that include a coupler that shields against electromagnetic interference (EMI).

2. Background Information

Near-infrared spectroscopy (NIRS) is an optical spectrophotometric method that can be used to continuously monitor tissue oxygenation. NIRS is based on the principle that light in the near-infrared range (700 nm to 1,000 nm) can pass easily through skin, bone and other tissues where it encounters hemoglobin located mainly within micro-circulation passages; e.g., capillaries, arterioles, and venuoles. Hemoglobin exposed to light in the near-infrared range has specific absorption spectra that varies depending on its oxidation state; i.e., oxyhemoglobin ($HbO_2$) and deoxyhemoglobin (Hb) each act as a distinct chromophore. NIRS involves transmitting near-infrared light at specific different wavelengths, and measuring changes in transmitted or reflected light attenuation. NIRS enables concentration changes of the oxyhemoglobin ($HbO_2$) and deoxyhemoglobin (Hb) to be monitored. The ability to continually monitor cerebral oxygenation levels, for example, is particularly valuable for patients who are subject to a condition in which oxygenation levels may be compromised.

NIRS systems have been developed that include at least one NIRS sensor assembly, a base unit, and at least one interface cable for connecting the NIRS sensor assembly to the base unit. Each NIRS sensor assembly typically includes at least one light source and at least one light detector, and is operable to generate a detection light signal that is communicated to the base unit for processing. Detection light signals are sent from each NIRS sensor assembly to the base unit of the NIRS system via an interface cable.

A problem common to all NIRS systems is EMI from external sources. EMI can negatively affect the quality of the detection light signal. These problems are not limited NIRS systems; the same or similar problems exist in other signal monitoring systems. What is needed, therefore, is an improved signal monitoring system directed toward these and other problems.

SUMMARY OF THE INVENTION

According to an aspect of the present invention, an apparatus for electrically and mechanically coupling a connection portion of a sensor assembly with a connection portion of an interface cable is provided. The apparatus includes a frame having an EMI shielding material. The frame defines a first port operable to engage the connection portion of the sensor assembly and a second port operable to engage the connection portion of the interface cable. The frame includes attachment features operable to mechanically secure the connection portion of the sensor assembly and the connection portion of the interface cable relative to the frame. The frame is configured to provide a Faraday Cage around substantially all of the connection portion of the sensor assembly and the connection portion of the interface cable when the connection portions are in coupled configuration.

According to another aspect of the present invention, an apparatus for sensing a biological characteristic of a subject is provided. The apparatus includes a sensor assembly, a base unit, and a coupler. The sensor assembly is operable to be attached to the subject, and is operable to produce electrical signals indicative of the biological characteristic being sensed. The sensor assembly includes a connection portion. The base unit includes a processor, and is operable to receive the electrical signals from the sensor assembly through an interface cable. The interface cable includes a connection portion. The coupler includes a frame having an EMI shielding material. The frame defines a first port operable to engage the connection portion of the sensor assembly and a second port operable to engage the connection portion of the interface cable. The frame includes attachment features operable to mechanically secure the connection portion of the sensor assembly and the connection portion of the interface cable relative to the frame. The frame is configured to provide a Faraday Cage around substantially all of the connection portion of the sensor assembly and the connection portion of the interface cable when the connection portions are in coupled configuration.

These and other objects, features, and advantages of the present invention apparatus and systems will become apparent in light of the detailed description of the invention provided below and the accompanying drawings. The apparatus and system described below constitutes a preferred embodiment of the underlying invention and does not, therefore, constitute all aspects of the invention that will or may become apparent by one of skill in the art after consideration of the invention disclosed overall herein.

DETAILED DESCRIPTION OF THE INVENTION

Figure 1:
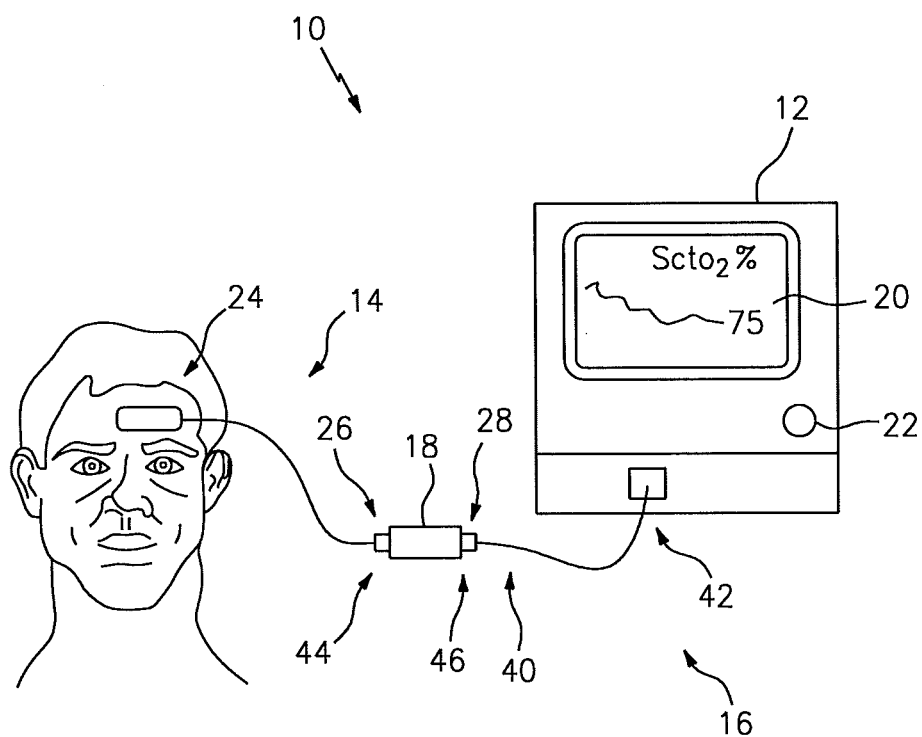
FIG. 1 is a diagrammatic representation of an embodiment of the present signal monitoring system, with a NIRS sensor assembly applied to a subject.

FIG. 1 illustrates a signal monitoring system 10 that includes a base unit 12, a NIRS sensor assembly 14, an interface cable 16, and a coupler 18. In alternative embodiments, the signal monitoring system 10 may include a plurality of NIRS sensor assemblies 14, a plurality of interface cables 16, and/or a plurality of couplers 18. In some embodiments, the signal monitoring system 10 may also include one or more different types of sensor assemblies for signal monitoring; e.g., a sensor assembly that is of a type that is not a NIRS sensor type assembly. For ease of description, however, aspects of the present invention will be described in terms of the signal monitoring system 10 illustrated in FIG. 1, which has a single NIRS sensor assembly 14, a single interface cable 16, and a single coupler 18.

The base unit 12 includes a display 20, operator controls 22, and a processor for providing signals to and/or receiving signals from the NIRS sensor assembly 14. The processor is adapted (e.g., programmed) to selectively perform the functions necessary to operate the NIRS sensor assembly 14, including processing signals to and from the sensor assembly 14, to create useful data. The functionality of the processor may be implemented using hardware, software, firmware, or a combination thereof. A person skilled in the art would be able to program the processor to perform the functionality described herein without undue experimentation. In embodiments in which the signal monitoring system 10 includes more than one NIRS sensor assembly 14, the base unit 12 is adapted to selectively perform the functions necessary to operate the NIRS sensor assemblies 14, including processing signals to and from the NIRS sensor assemblies 14, to create useful data.

The NIRS sensor assembly 14 includes a sensor portion 24 and a connection portion 26. In some embodiments, the NIRS sensor assembly 14 may additionally include pads, housings, EMI shielding, or other features, including, for example, the features described in International Patent Application No. PCT/US12/24889, which is hereby incorporated by reference. Such additional features will not be described in detail herein.

The sensor portion 24 of the NIRS sensor assembly 14 includes at least one light source. The light source is selectively operable to guide or emit infrared light (e.g., light in wavelength range of about 700 nm to about 1,000 nm), but is not limited to infrared light. For example, in some embodiments the sensor may include a light source that is operable to produce light at wavelengths outside the infrared range (e.g., in the range between 400 nm and 700 nm, or both visible and infrared light combinations, etc). The NIRS sensor assembly 14 is not limited to use with any particular type of light source embodiment. International Patent Application No. PCT/US12/24889, incorporated by reference hereinabove, discloses that acceptable light sources include light emitting diodes (LEDs), light transmitted through a fiber optic light guide, etc. As will be discussed further below, the light source may be mounted on a flexible electrical circuit disposed within the body 25 of the sensor portion 24 of the NIRS sensor assembly 14.

The sensor portion 24 of the NIRS sensor assembly 14 further includes at least one light detector (e.g., a photodiode) that is operable to sense light emitted by the light source after such light passes through a portion of a subject's body. The light detector is operable to generate what will hereinafter be referred to as the "detection light signal". The detection light signal is indicative of the light sensed by that light detector, and the detection light signal is communicated to the base unit 12 of the signal monitoring system 10 for processing. The NIRS sensor assembly 14 is not limited to use with any particular light detector embodiment.

The connection portion 26 of the NIRS sensor assembly 14 is configured for mechanical connection with the coupler 18, and electrical and mechanical connection with a connection portion 28 of the interface cable 16, as will be explained below. The term "cable" as used herein, and except as further described herein, is defined to mean a bound group of one or more insulated electrical conductors.

Figure 2:
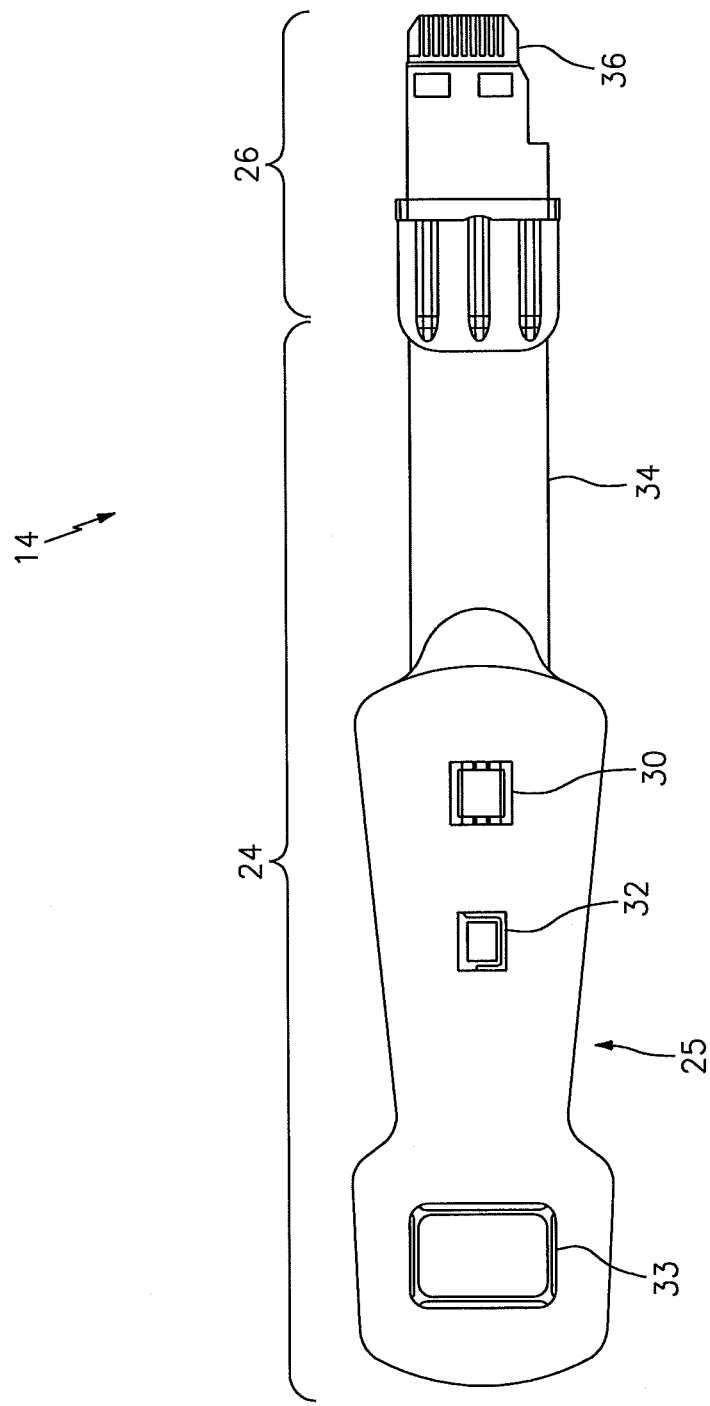
FIG. 2 is a diagrammatic plan view of a NIRS sensor assembly.

In an embodiment of a NIRS sensor assembly 14 shown in FIG. 2, the NIRS sensor assembly 14 includes a sensor portion 24 having a light source 30 and two light detectors 32, 33 mounted on a flexible electrical circuit disposed within the body 25 of the sensor portion 24. A lead portion 34 of the flexible electrical circuit extends out from the body 25 of the sensor portion 24, and extends to the connection portion 26 of the NIRS sensor assembly 14. Alternatively, a cable may be attached to the flexible electrical circuit disposed within the body 25 of the sensor portion 24, which cable extends to the connection portion 26. The connection portion 26 may include a printed circuit board card 36 (i.e., a "PCB card"). The light source 30 and the light detectors 32, 33 are mounted proximate one end of the flexible electrical circuit, and the PCB card 36 is mounted to the opposing end of the flexible electrical circuit. The NIRS sensor assembly 14 is not limited to the embodiment illustrated in FIG. 2; e.g., in other embodiments, the sensor portion 24 of the NIRS sensor assembly 14 need not include a flexible electrical circuit, and the connection portion 26 need not include a PCB card 36.

Referring again to FIG. 1, the interface cable 16 includes a first end portion 40 and an opposing second end portion 42. The first end portion 40 of the interface cable 16 includes the connection portion 28 that is configured to mechanically connect with the coupler 18, and electrically and mechanically connect with the connection portion 26 of the NIRS sensor assembly 14. The connection portion 28 of the interface cable 16 includes an electromechanical connector 66, such as a DisplayPort type connector, for electromechanical connection with the connection portion 26 of the NIRS sensor assembly 14. The connection portion 28 is not, however, limited to a DisplayPort type connector, and may alternatively use other types of electromechanical connectors; e.g., commercially available or custom electromechanical connectors. In some embodiments, the connection portion 28 may include mating attachment features configured to mate with the coupler 18. The second end portion 42 of the interface cable 16 is connected to the base unit 12 of the signal monitoring system 10.

Referring to FIGS. 1, and 3-7, the coupler 18 electrically and mechanically connects the NIRS sensor assembly 14 with the interface cable 16. The coupler 18 includes an internal frame 19, and preferably includes a housing 82. The coupler 18 may be described as having a length extending along the x-axis, a width extending along the y-axis, and a height extending along the z-axis (e.g., see FIG. 5). The frame 19 includes one or more walls that define a first port 44 and a second port 46. The first port 44 is configured to receive the connection portion 26 of the NIRS sensor assembly 14. The second port 46 is configured to receive the connection portion 40 of the interface cable 16. The frame walls are formed from, or include, at least one EMI shielding material, and the walls collectively form a Faraday Cage. For example, the frame 19 may be made from a stainless steel material, or an electrically conductive wire mesh (e.g., copper wire mesh), or combinations thereof. The frame 19 material is not, however, limited to these materials. In some embodiments, an EMI shielding material can also be partially or completely wrapped around the frame 19 to provide additional EMI shielding. An example of an acceptable electrically conductive tape is XYZ-Axis Electrically Conductive Tape 9713, offered by 3M Company of St. Paul, Minn., USA. The EMI shielding material is not, however, limited to this example. An electrically conductive, fiber-filled adhesive tape (e.g., the 9713 Tape) provides several advantages, including: (1) it is relatively inexpensive; (2) it does not require a soldered connection to ground; (3) it is available in roll form; (4) it has a low profile; and (5) it is flexible. The frame 19 is configured so that, in a "coupled configuration", shown for example in FIG. 1 and discussed further below, the connection portion 26 of the NIRS sensor assembly 14 and the connection portion 28 of the interface cable 16 are at least partially disposed within a Faraday Cage.

Figure 3:
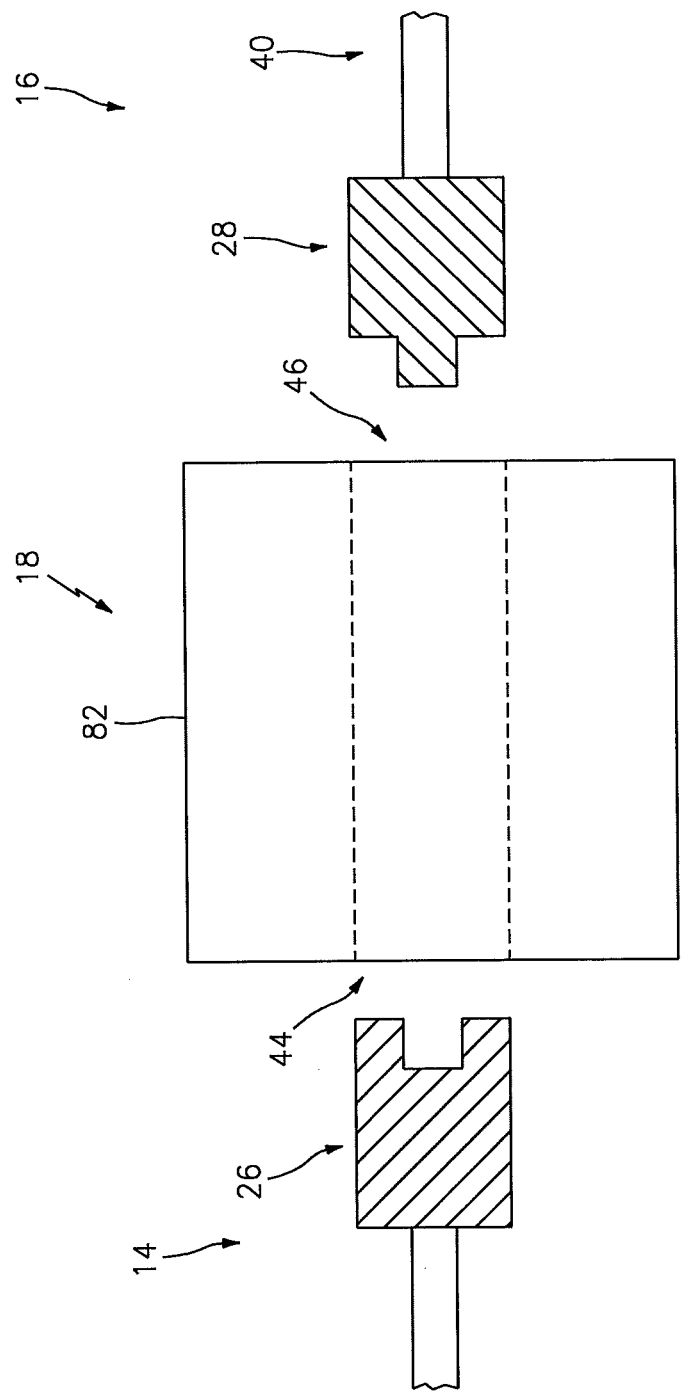
FIG. 3 is a diagrammatic illustration of the coupler, with the NIRS sensor assembly connection portion and the interface cable connection portion depicted in an uncoupled configuration.
Figure 4:
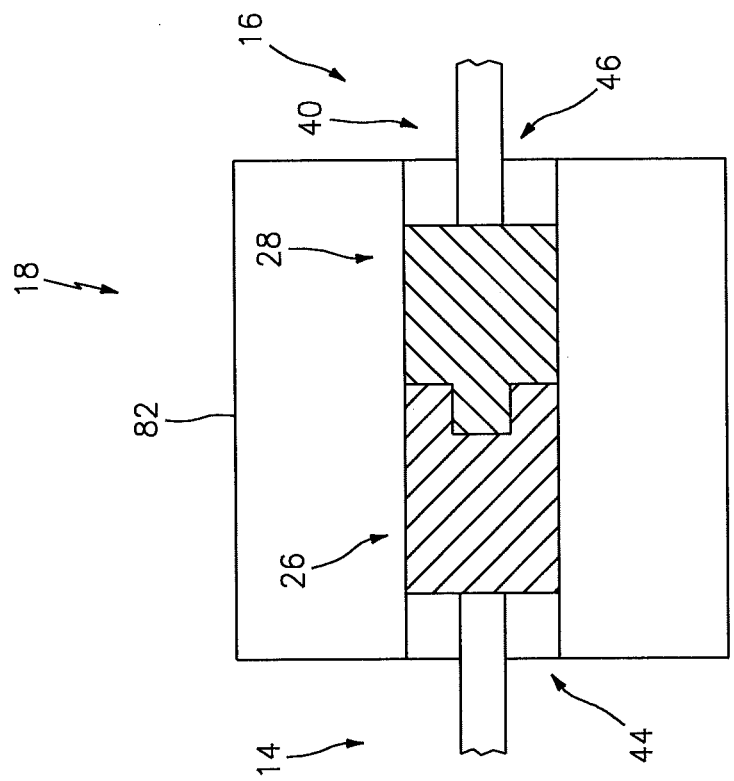
FIG. 4 is a diagrammatic illustration of the coupler, with the NIRS sensor assembly connection portion and the interface cable connection portion depicted in a coupled configuration.

FIGS. 3 and 4 illustrate the difference between an "uncoupled configuration" and a "coupled configuration". FIG. 3 illustrates the NIRS sensor assembly 14, the interface cable 16, and the coupler 18 in an "uncoupled configuration". In FIG. 3, the connection portion 26 of the NIRS sensor assembly 14 is not inserted into the first port 44 of the coupler 18, and the connection portion 28 of the first end portion 40 of the interface cable 16 is not inserted into the second port 46 of the coupler 18. FIG. 4 illustrates the NIRS sensor assembly 14, the interface cable 16, and the coupler 18 in a "coupled configuration", wherein the connection portions 26, 28 are electrically and mechanically connected; i.e., the connection portion 26 of the NIRS sensor assembly 14 is inserted into the first port 44 of the coupler 18, and the connection portion 46 of the first end portion 40 of the interface cable 16 is inserted into the second port 46 of the coupler 18. In FIGS. 3 and 4, the connection portions 26, 28 are diagrammatically shown as mating male and female connectors. The connection portions 26, 28 are not limited to mating male and female connectors, however. In addition, the connection portions 26, 28 need not be directly connected to one another as shown in FIGS. 3 and 4; e.g., in some embodiments, the coupler 18 may include structure that electrically and mechanically connects the two connection portions 26, 28.

Figure 5:
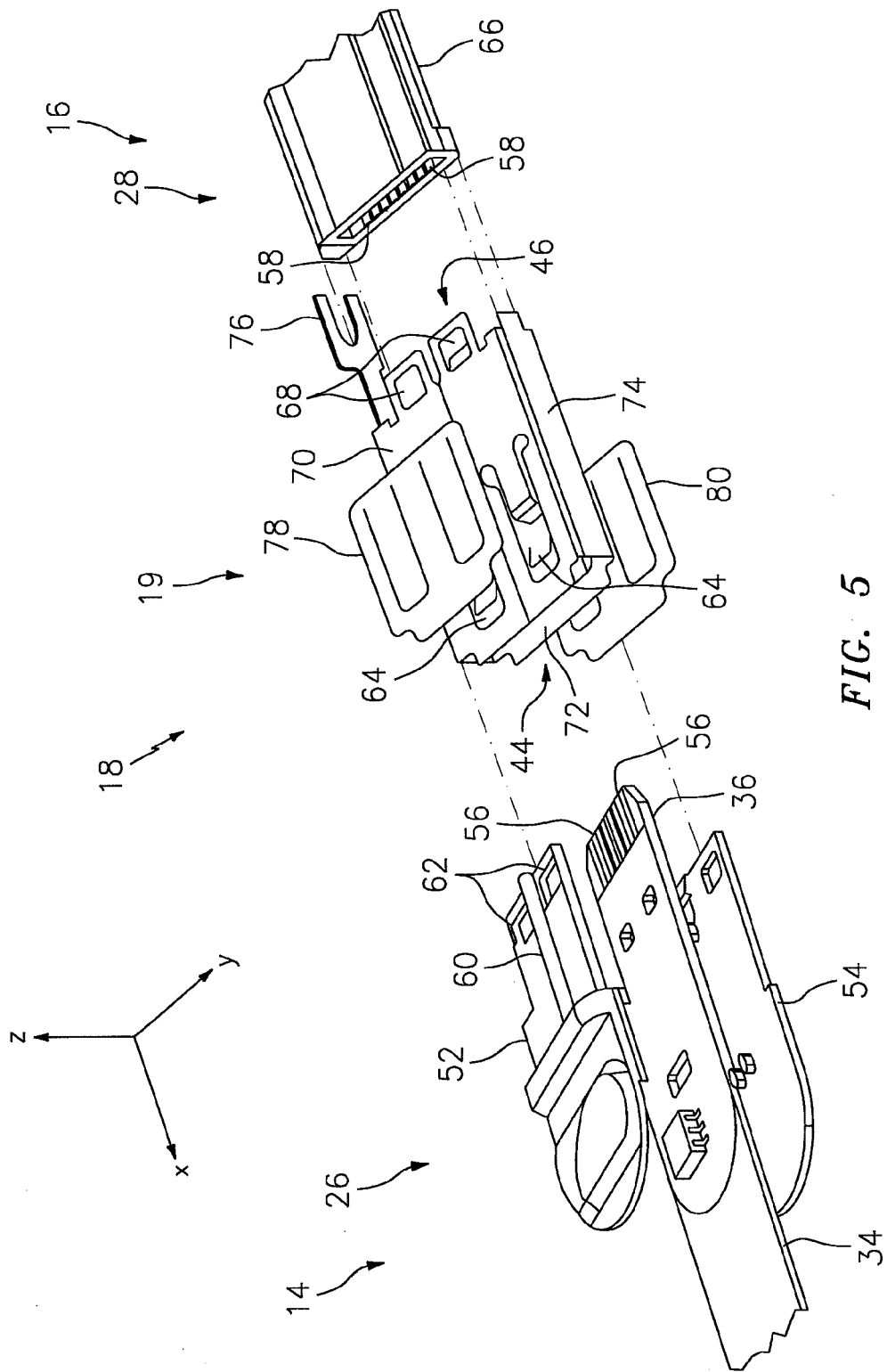
FIG. 5 is a diagrammatic exploded view of the coupler, the NIRS sensor assembly connection portion, and the interface cable connection portion.

FIG. 5 illustrates an exploded view of an embodiment of the coupler 18 with the housing 82 omitted to facilitate the description, together with the connection portion 26 of the NIRS sensor assembly 14 and the connection portion 28 of the interface cable 16. In FIG. 5, the NIRS sensor assembly 14, the interface cable 16, and the coupler 18 are in an "uncoupled configuration". In the embodiment illustrated in FIG. 5, the connection portion 26 includes a PCB card 36, a top body portion 52, and a bottom body portion 54. The PCB card 36 includes a plurality of leads 56, each operable to mechanically and electrically connect with a corresponding port 58 on the connection portion 28 of the interface cable 16, as will be discussed further detail below. The top and bottom body portions 52, 54 are attached to the PCB card 36, for example, using one or more mechanical fasteners, ultrasonic welding, adhesives, or other means for attaching, including a molding process. In the embodiment illustrated in FIG. 5, the connection portion 26 is operable to be received by the first port 44 of the coupler 18. In the embodiment illustrated in FIG. 5, the top body portion 52 includes an alignment feature 60 operable to engage with a corresponding alignment feature of the coupler 18 (not visible in FIG. 5). The alignment feature 60 is operable to aid in alignment as the connection portion 26 is received by the first port 44 of the coupler 18. The top and bottom body portions 52, 54 may be made of plastic or other non-electrically-conductive material.

In the embodiment shown in FIG. 5, the top body portion 52 includes mating attachment features 62 (e.g., clips, etc.) operable to engage corresponding mating attachment features 64 in the frame 19. In some embodiments, both the top and bottom body portions 52, 54 may include mating attachment features operable to engage corresponding mating attachment features in the frame 19. The engagement of mating attachment features 62 of one or both of the body portions 52, 54 with the corresponding mating attachment features 64 of the frame 19 may form a snap fit, a compression fit, or the like. The engagement of mating attachment features of the body portions 52, 54 and the frame 19 can be configured to create a sound (e.g., a snapping or clicking) that is an audible indication to the user that the connection has been made. The engagement of mating attachment features 62 of the body portions 52, 54 with the corresponding mating attachment features 64 of the frame 19 can also be configured to bias the body portions 52, 54 and the coupler 18 together with a predetermined retention force. The magnitude of the retention force may be selected to suit the application at hand; e.g., the mating attachment features may be configured to create a retention force equal to, greater than, or less than the force with which sensor portion 24 of the NIRS sensor assembly 14 is attached to the subject being monitored. For example, in some embodiments, the sensor portion 24 of the NIRS sensor assembly 14 includes an adhesive that requires a force of "N" pounds applied (e.g., laterally applied) to remove the sensor portion 24 from the subject being monitored. The aforesaid retention force that biases the body portions 52, 54 together with the coupler 18 may be selected so that the retention force is equal to, greater than, or less than force necessary to remove the sensor portion 24 of the NIRS sensor assembly 14 from the subject being monitored.

In the embodiment shown in FIG. 5, the connector 66 within the connection portion 28 of the interface cable 16 is a DisplayPort type connector. The connector 66 includes attachment features (not shown in FIG. 5) that engage corresponding attachment features 68 of the coupler 18. In some embodiments, the attachment features may be "mating" features; e.g, male and female, etc. The connector 66 includes a plurality of ports 58, each operable to mechanically and electrically connect with a corresponding lead 56 on the PCB card 36 of the connection portion 26 of the NIRS sensor assembly 14.

In the embodiment illustrated in FIG. 5, the internal frame 19 has a rectangular configuration that includes a top wall 70, a bottom wall 72, a first side wall 74, a second side wall 73. The first side wall 74 and the second side wall 73 extend in a height wise direction between the top wall 70 and the bottom wall 72. The four walls of the frame 19 define an internal cavity. The term "cavity" is used herein to mean a void or an open space. The four walls of the frame 19 also define at least a portion of the first port 44 and the opposing second port 46. As indicated above, the four walls of the frame 19 collectively form a Faraday Cage. The cavity defined by the four walls of the frame 19 may be described as being the inside the Faraday Cage. The present coupler 18 is not limited to the rectangular configuration shown in FIG. 5 (e.g., having a plurality of walls 70, 72, 73, 74) and may, for example include a cylindrical configuration having a single wall.

Referring still to FIG. 5, the top wall 70 of the frame 19 includes mating features 64 proximate the first port 44. The mating attachment features 64 are configured to mate with the corresponding mating attachment features 62 on the top body portion 52. For example, the specific embodiment shown in FIG. 5 illustrates mating attachment features 64 in the form of clips that are configured to engage mating attachment features 62 in the form of apertures or depressions in the top body portion 52. The top wall 70 of the frame 19 also includes mating attachment features 68 proximate the second port 46 which are configured to mate with corresponding mating attachment features included in the connection portion 28 of the interface cable 16 (not visible in FIG. 5); e.g., the same as or similar to those shown for mating attachment features 62, 64. The frame 19 can include an alignment feature (not visible in FIG. 5) operable to engage the corresponding alignment feature 60 of the top body portion 52 of the connection portion 26 of the NIRS sensor assembly 14. The corresponding alignment features aid in correct alignment between the connection portion 26 of the NIRS sensor assembly 14 and the coupler 18 during connection. In the embodiment illustrated in FIG. 5, the frame 19 includes a slotted tab 76 extending from the second side wall. The slotted tab 76 is configured for connection with a ground terminal; e.g., via a ring terminal.

Pieces of tape 78, 80 (e.g., 9713 Tape) may be attached to the top wall 70 and bottom wall 72 of the frame 19, respectively, to cover openings in the top and bottom walls 70, 72 of the frame 19, or to cover the entire frame 19 as described above.

In operation of the coupler 18 embodiment illustrated in FIG. 5, the connection portion 26 of the NIRS sensor assembly 14 can be moved in a lengthwise direction until it is inserted into the first port 44 of coupler 18. The mating attachment features 62 of the top body portion 52 slidably engage the corresponding mating attachment features 64 of the frame 19 to retain the two elements together. In similar fashion, the connection portion 28 of the interface cable 16 can be moved in a lengthwise direction until it is inserted into the second port 46 of the coupler 18. The mating features of the connection portion 28 of the interface cable 16 (not shown in FIG. 5) slidably engage the corresponding mating attachment features 68 of the frame 19 to retain the two elements together. In this coupled configuration, each of the leads 56 on the PCB card 36 of the connection portion 26 mechanically and electrically connect with corresponding ports 58 in the connector 66 of connection portion 28, and at least a portion of the connection portions 26, 28 are disposed within the cavity. As discussed above, the cavity is inside the Faraday Cage defined by the four walls of the internal frame 19. Thus, in this coupled configuration, at least a portion of the connection portions 26, 28 are disposed within the Faraday Cage. As a result, the point of contact between the NIRS sensor assembly 14 and the interface cable 16 is shielded against EMI.

Figure 6:
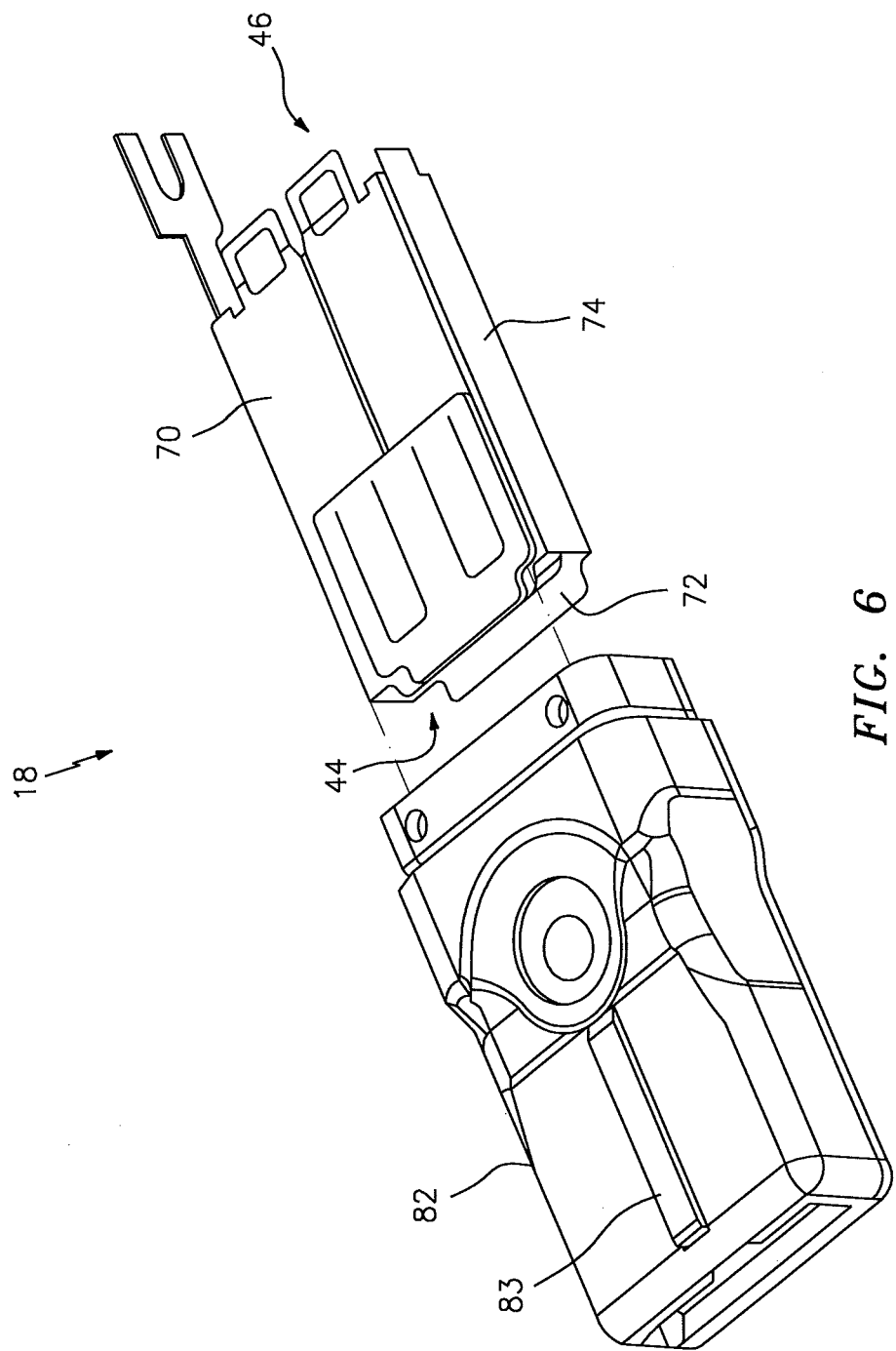
FIG. 6 is a diagrammatic exploded view of the coupler.

The exploded view of FIG. 6 illustrates the internal frame 19 described above with regard to FIG. 5 (i.e., the top wall 70, the bottom wall 72, the first side wall 74, and the second side wall), and the housing 82 of the coupler 18. The housing 82 is configured to enclose the four walls of the frame 19. The housing 82 is preferably made of plastic or some other non-electrically-conductive material. The housing 82 may be constructed using one or more pieces. The housing 82 may be configured so that when the connection portion 26 of the NIRS sensor assembly 14 is received within the first port 44 of the coupler 18, a seal is formed between the housing 82 and the connection portion 26 of the NIRS sensor assembly 14, thereby preventing liquid and/or gas from entering the first port 44 of the coupler 18. In the embodiment illustrated in FIG. 6, the housing 82 includes an orientation feature 83 operable to indicate the orientation of the coupler 18 to the user; e.g., the orientation feature 83 may indicate the correct orientation of the housing 82 relative to the connection portion 26 of the NIRS sensor assembly 14. The coupler 18 is not limited to the housing 82 embodiment illustrated in FIG. 6.

Figure 7:
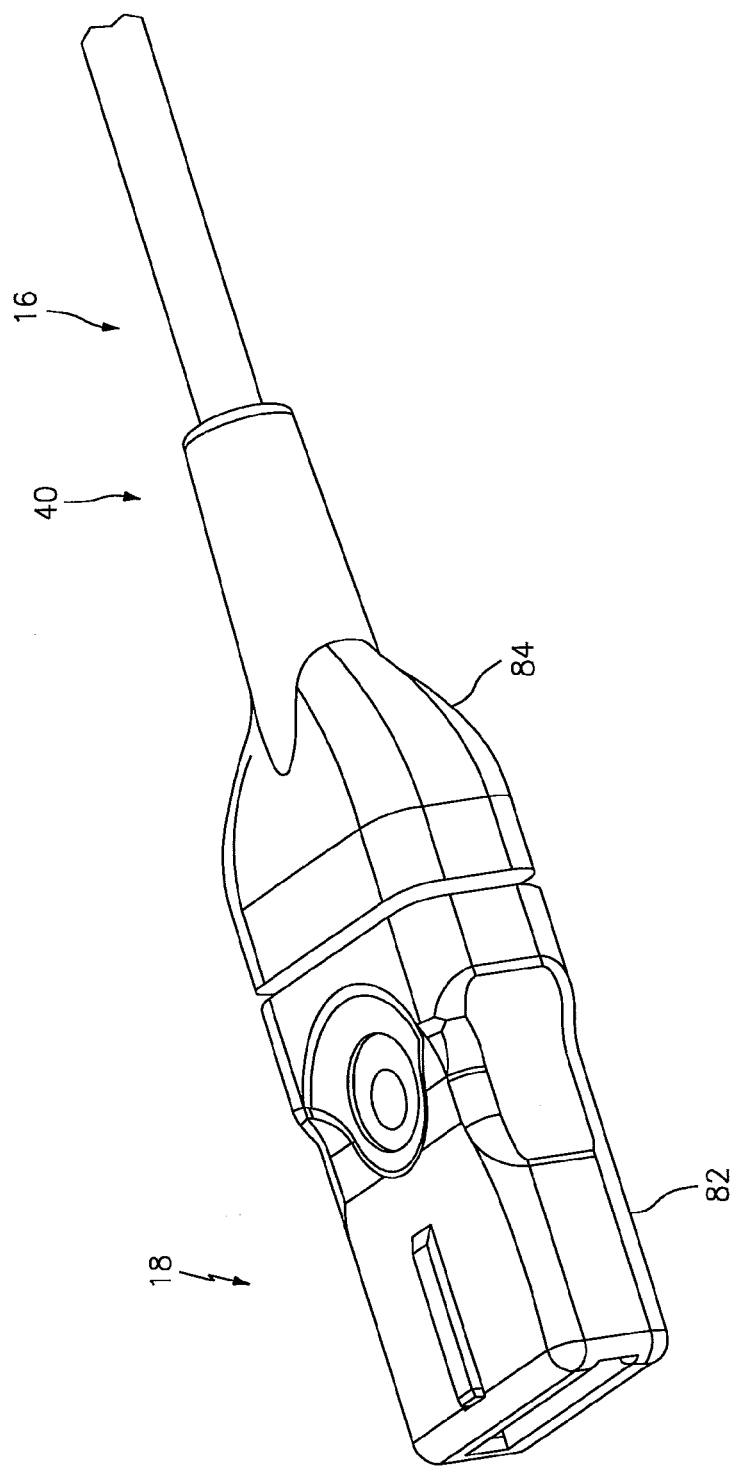
FIG. 7 is a diagrammatic view of the coupler joined with the interface cable connection portion as a unitary structure.

FIG. 7 illustrates an embodiment of the coupler 18, wherein the housing 82 encloses the four walls of the internal frame 19 (i.e., the top wall 70, the bottom wall 72, the first side wall 74, and the second side wall) and the connection portion 28 of the interface cable 16 is permanently received within the second port 46 of the coupler 18. In this embodiment, the first end portion 40 of the interface cable 16 is disposed within an extension 84 of the housing 82.

Referring again to FIG. 1, in the operation of the signal monitoring system 10, once the NIRS sensor assembly 14 is positioned relative to the subject's skin, the NIRS sensor assembly 14 is used to introduce light signals into the subject's body tissue. The light introduced into the subject's body tissue is subsequently detected and a detection light signal is generated. The detection light signal is relayed back to the base unit 10 via the interface cable 16, where the detection light signal is processed and analyzed to obtain data; e.g., relating to the oxygenation level of the subject's body tissue. The coupler 18 prevents EMI from being introduced to the detection light signal at the point of contact between the NIRS sensor assembly 14 and the interface cable 16.

While various embodiments of the present invention have been disclosed, it will be apparent to those of ordinary skill in the art that many more embodiments and implementations are possible within the scope of the invention. For example, embodiments of the connection portion of the sensor assembly are described above including a printed circuit board, and embodiments of the interface cable are described above as including a DisplayPort connector. In alternative embodiments, the PCB and the DisplayPort connector can be attached to the other of the interface cable and the sensor assembly respectively; i.e., switched vice versa. Accordingly, the present invention is not to be restricted except in light of the attached claims and their equivalents.

What is claimed is:

1. An apparatus for electrically and mechanically coupling a connection portion of a sensor assembly with a connection portion of an interface cable, comprising:
   a frame having an EMI shielding material, which frame defines a first port operable to engage the connection portion of the sensor assembly and a second port operable to engage the connection portion of the interface cable;
   wherein the frame includes attachment features operable to mechanically secure the connection portion of the sensor assembly and the connection portion of the interface cable relative to the frame; and
   wherein the frame is configured to provide a Faraday Cage around substantially all of the connection portion of the sensor assembly and the connection portion of the interface cable when the connection portions are in coupled configuration; and
   wherein the connection portion of one of the interface cable and the sensor assembly includes a printed circuit board, and the other of the interface cable and the sensor assembly includes a DisplayPort connector.

2. The apparatus of claim 1, wherein the apparatus further comprises a housing configured to enclose the frame, which housing is formed of an electrically non-conductive material.

3. The apparatus of claim 1, wherein the frame is configured to form an internal cavity surrounded by one or more walls, and a first end of the cavity defines the first port and is configured to receive the connection portion of the sensor assembly, and an opposing second end of the cavity defines the second port and is configured to receive the connection portion of the interface cable.

4. The apparatus of claim 3, wherein the cavity is configured such that the frame walls surround substantially all of the connection portion of the sensor assembly and the connection portion of the interface cable when the connection portions are in coupled configuration.

5. The apparatus of claim 4, wherein the walls include the attachment features operable to mechanically secure the connection portion of the sensor assembly and the connection portion of the interface cable relative to the frame.

6. The apparatus of claim 5, wherein the attachment features are positioned to maintain a mechanical and electrical connection between the connection portions.

7. The apparatus of claim 6, wherein the attachment features are positioned to bias the connection portions together.

8. The apparatus of claim 6, wherein the attachment features are configured such that a predetermined amount of force is required to separate one or both of the connection portions from the frame.

9. The apparatus of claim 8, wherein the predetermined amount of force is equal to or less than an amount of force required to remove the sensor assembly adhered to a subject.

10. The apparatus of claim 6, wherein the cavity is configured such that the frame walls surround substantially all of the printed circuit board and the DisplayPort connector when they are in coupled configuration.

11. An apparatus for sensing a biological characteristic of a subject, comprising:
- a sensor assembly operable to be attached to the subject, which sensor assembly is operable to produce electrical signals indicative of the biological characteristic being sensed, and which sensor assembly includes a connection portion;
- a base unit having a processor, which base unit is operable to receive the electrical signals from the sensor assembly through an interface cable, and which interface cable includes a connection portion; and
- a coupler that includes a frame having an EMI shielding material, which frame defines a first port operable to engage the connection portion of the sensor assembly and a second port operable to engage the connection portion of the interface cable, wherein the frame includes attachment features operable to mechanically secure the connection portion of the sensor assembly and the connection portion of the interface cable relative to the frame, and wherein the frame is configured to provide a Faraday Cage around substantially all of the connection portion of the sensor assembly and the connection portion of the interface cable when the connection portions are in coupled configuration.

12. The apparatus of claim 11, wherein the coupler further comprises a housing configured to enclose the frame, which housing is formed of an electrically non-conductive material.

13. The apparatus of claim 11, wherein the frame is configured to form an internal cavity surrounded by one or more walls, and a first end of the cavity defines the first port and is configured to receive the connection portion of the sensor assembly, and an opposing second end of the cavity defines the second port and is configured to receive the connection portion of the interface cable.

14. The apparatus of claim 13, wherein the cavity is configured such that the frame walls surround substantially all of the connection portion of the sensor assembly and the connection portion of the interface cable when the connection portions are in coupled configuration.

15. The apparatus of claim 14, wherein the walls include the attachment features operable to mechanically secure the connection portion of the sensor assembly and the connection portion of the interface cable relative to the frame.

16. The apparatus of claim 15, wherein the attachment features are positioned to maintain a mechanical and electrical connection between the connection portions.

17. The apparatus of claim 16, wherein attachment features are positioned to bias the connection portions together.

18. The apparatus of claim 16, wherein the attachment features are configured such that a predetermined amount of force is required to separate one or both of the connection portions from the frame.

19. The apparatus of claim 18, wherein the predetermined amount of force is equal to or less than an amount of force required to remove the sensor assembly adhered to a subject.

20. The apparatus of claim 16, wherein the connection portion of one of the interface cable and the sensor assembly includes a printed circuit board, and the other of the interface cable and the sensor assembly includes a DisplayPort connector, and the cavity is configured such that the frame walls surround substantially all of the printed circuit board and the DisplayPort connector when they are in coupled configuration.

* * * * *